United States Patent [19]

Lee et al.

[11] Patent Number: 4,894,465

[45] Date of Patent: Jan. 16, 1990

[54] INTERMEDIATES AND PROCESSES FOR 6-HYDROXYMETHYL HMG-COA REDUCTABLE INHIBITORS

[75] Inventors: Ta J. Lee; William F. Hoffman, both of Lansdale, Pa.

[73] Assignee: Merck & Co., Inc., Rahway, N.J.

[21] Appl. No.: 161,530

[22] Filed: Feb. 29, 1988

[51] Int. Cl.$^4$ ............................................. C07D 309/30
[52] U.S. Cl. ..................................... 549/214; 549/292; 544/59; 544/60; 544/149; 544/359; 544/389; 546/207; 546/245; 548/518; 548/531
[58] Field of Search ................. 549/292, 214; 514/460

[56] References Cited

U.S. PATENT DOCUMENTS 4,444,784  4/1984  Hoffman et al. ..................... 549/292
4,582,915  4/1986  Sleteinger et al. .................. 549/292

Primary Examiner—Richard L. Raymond
Assistant Examiner—Ba K. Trinh
Attorney, Agent, or Firm—Melvin Winokur; Joseph F. DiPrima

[57] ABSTRACT

This invention discloses intermediates and processes for the preparation of 6-desmethyl-6-α hydroxymethyl derivatives of lovastatin and analogs thereof at the 8-acyl side chain.

4 Claims, No Drawings

INTERMEDIATES AND PROCESSES FOR 6-HYDROXYMETHYL HMG-COA REDUCTABLE INHIBITORS

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time and they are not very palatable.

MEVACOR® (lovastatin), now commercially available, is one of a group of very active antihypercholesterolemic agents that function by limiting cholesterol biosynthesis by inhibiting the enzyme, HMG-CoA reductase. In addition to the natural fermentation products, mevastatin and lovastatin, there are a variety of semi-synthetic and totally synthetic analogs thereof.

The naturally occurring compounds and their semi-synthetic analogs have the following general structural formulae:

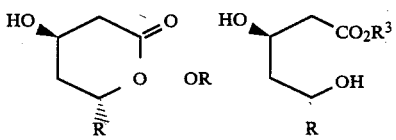

wherein:
$R^3$ is hydrogen, $C_{1-5}$ alkyl or $C_{1-5}$ alkyl substituted with a member of the group consisting of phenyl, dimethylamino, or acetylamino; and
$R^*$ is

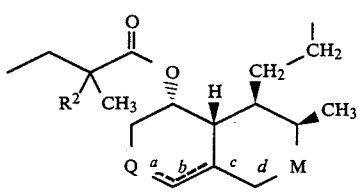

wherein Q is

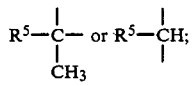

$R^5$ is H or OH; M is $-CHR^6$, $R^6$ is hydrogen or hydroxy;
$R^2$ is hydrogen or methyl; and a, b, c, and d represent single bonds, one of a, b, c or d represents a double bond, or both a and c or both b and d represent double bonds provided that when a is a double bond, Q is

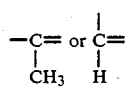

and when d is a double bond, M is $$=\overset{|}{\underset{H}{C.}}$$

U.S. Pat. No. 4,517,373 discloses semi-synthetic hydroxy containing compounds represented by the above general formula wherein $R^*$ is

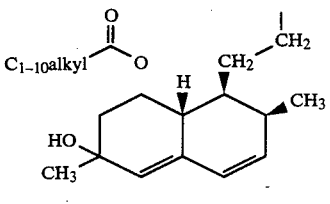

AND

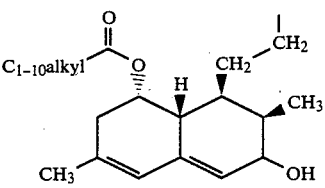

U.S. Pat. No. 4,537,859 and U.S. Pat. No. 4,448,979 also disclose semi-synthetic hydroxy-containing compounds represented by the above general formula wherein $R^*$ is

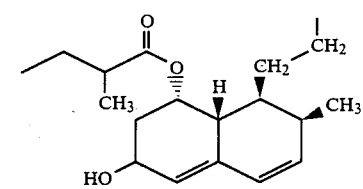

AND

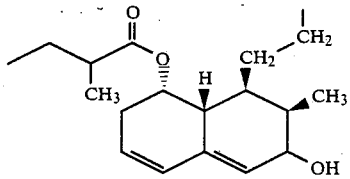

These compounds are prepared by the action of certain microorganisms on the corresponding non-hydroxylated substrates. One such organism described in U.S. Pat. No. 4,537,859 is of the genus Nocardia.

U.S. Pat. No. 4,376,863 discloses a fermentation product, isolated after cultivation of a microorganism belonging to the genus Aspergillus, which has a hydroxy containing butyryloxy side chain and is represented by the above general formula wherein $R^*$ is

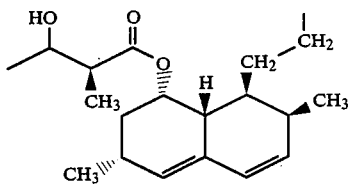

Japanese unexamined patent application J59-122,483-A discloses a semi-synthetic hydroxy-containing compound represented by the above general formula wherein R* is

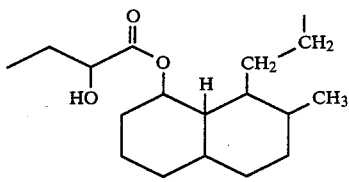

U.S. patent application Ser. No. 048,136 filed on May 15, 1987 discloses 6-substituted compounds of the above general formula wherein R* is

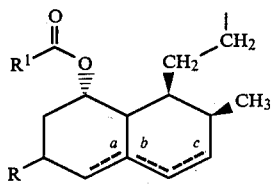

wherein R is CH$_2$OH,

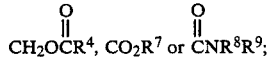

and R$^1$, R$^4$, R$^7$, R$^8$ and R$^9$ are broadly defined organic moieties.

The compounds of the above-mentioned U.S. patent application, Ser. No. 048,136 wherein a and c are double bonds were prepared by a microbiological conversion of lovastatin or an analog thereof with a 6-methyl substituent. Compounds where one of a, b or c represent a double bond or a, b, c all represent single bonds were prepared by a synthetic sequence from the 8-hydroxy-6-methyl derivative.

Copending U.S. application Ser. No. 131695 filed Dec. 11, 1987 discloses a process for the preparation of 6-desmethyl-6-carboxy derivatives of lovastatin and analogs thereof at the 8-acyl side chain.

The literature discloses a reaction known as the Barton Reaction by which a hydrogen on the γ carbon to a COH group can be abstracted to afford a carbon radical which can be oxidized. (See Hesse Adv. Free-Radical Chem. 3, 83–137 (1969); Barton, Pure Appl. Chem. 16, 1–15 (1968); Arthar, Adv. Photochem. 2, 263–304 (1964).

DETAILED DESCRIPTION OF THE INVENTION

This invention relates to novel intermediates, and novel processes for their preparation, where said intermediates are useful in a novel preparation of 6-desmethyl-6-α-hydroxymethyl (I) derivatives of lovastatin and analogs thereof at the 8-acyl side chain. Said 6-hydroxymethyl derivatives of lovastatin and analogs thereof are useful in treating hypercholesterolemia and are disclosed in copending patent application, Ser. No. 048,136 filed May 15, 1987.

The 6-desmethyl-6-α-hydroxymethyl (I) derivatives of lovastatin are prepared by related processes as shown in schemes 1 and 2. Schemes 1 and 2, which are both encompassed within the present invention, differ only in the timing sequence for the reduction of the halide moiety, in the 5-position of the octahydronaphthyl group, with a trialkyltin hydride.

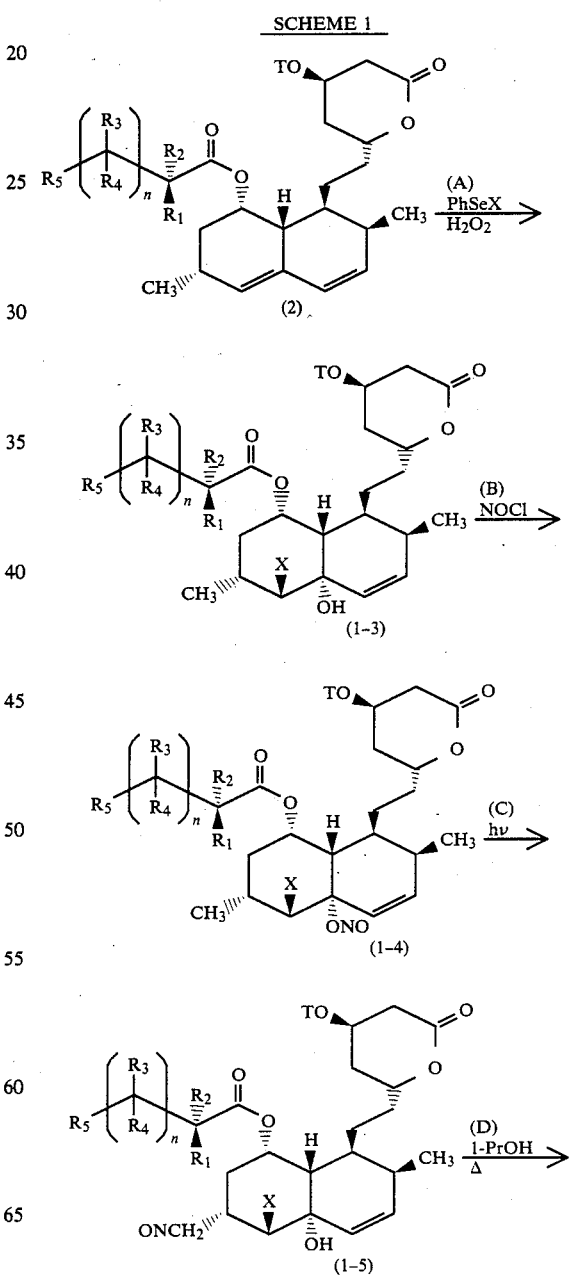

4,894,465
5
-continued
SCHEME 1
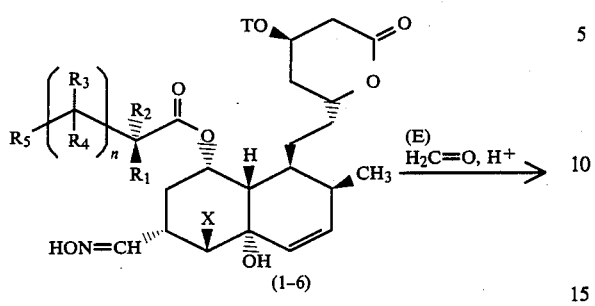
(1-6)
(E) H₂C=O, H⁺ →
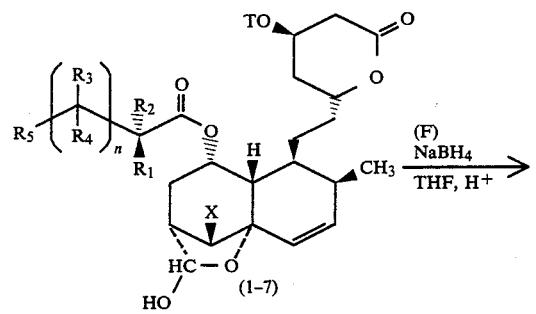
(1-7)
(F) NaBH₄ THF, H⁺ →
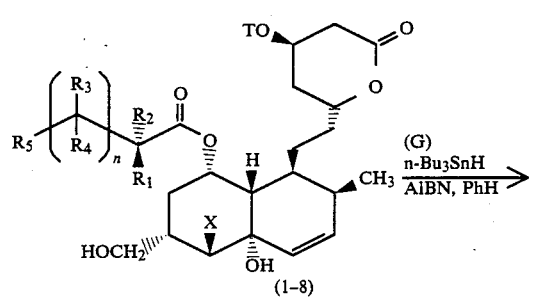
(1-8)
(G) n-Bu₃SnH AIBN, PhH →
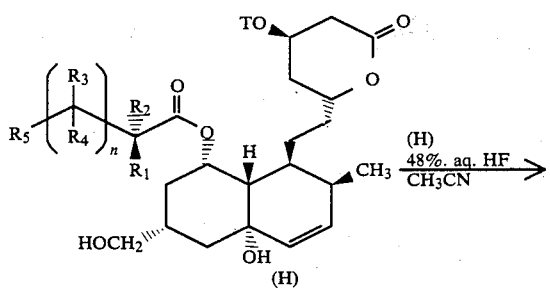
(H)
(H) 48%. aq. HF CH₃CN →
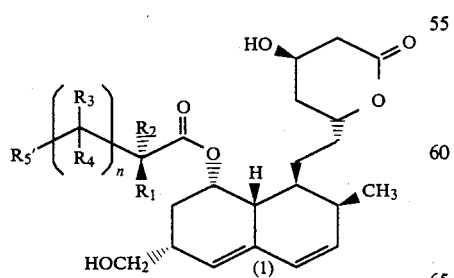
(1)
6
SCHEME 2
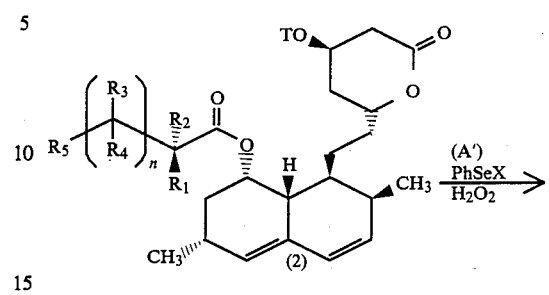
(2)
(A') PhSeX H₂O₂ →
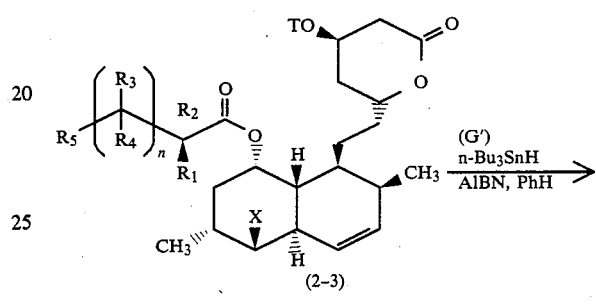
(2-3)
(G') n-Bu₃SnH AIBN, PhH →
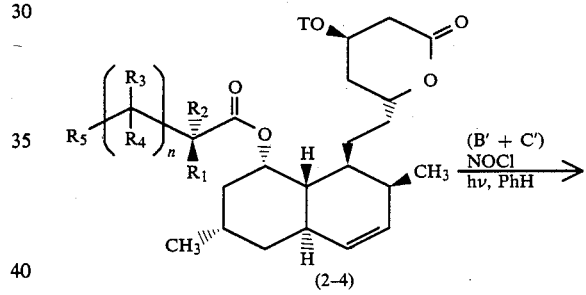
(2-4)
(B' + C') NOCl hν, PhH →
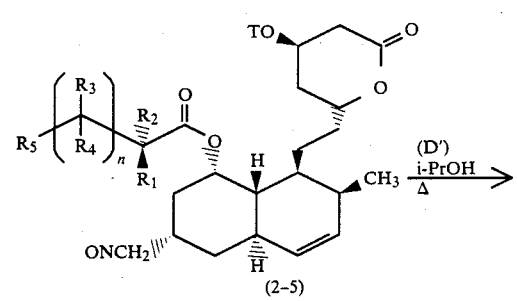
(2-5)
(D') i-PrOH Δ →
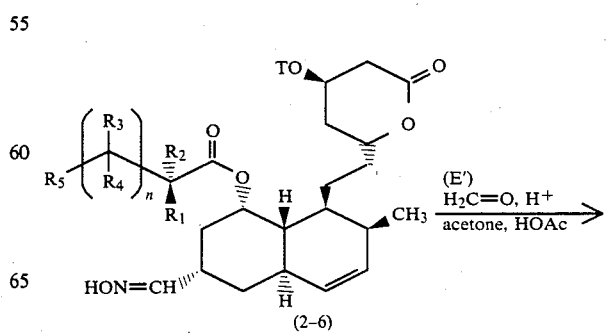
(2-6)
(E') H₂C=O, H⁺ acetone, HOAc →

-continued
SCHEME 2

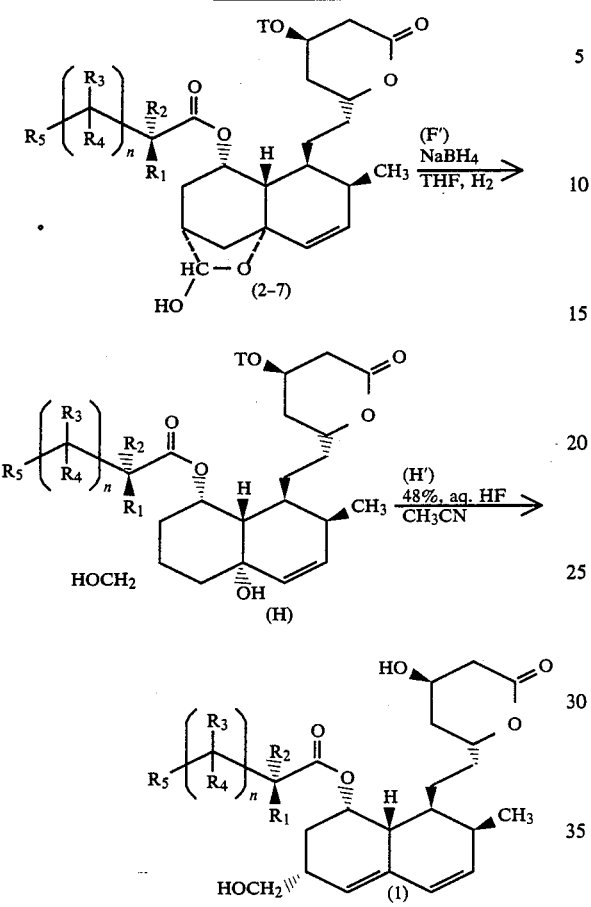

The products (I) of the instant invention can be prepared in a novel process as shown in Scheme 1 which comprises:
(A) contacting the compound (2)

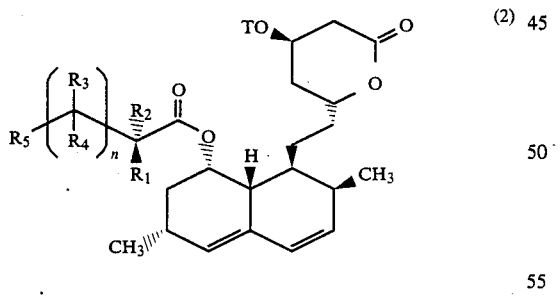

wherein:
n is 0 to 3;
$R_1$ and $R_2$ independently are hydrogen, $C_{1-5}$ alkyl, or $R_1$ and $R_2$ together with the carbon atom to which they are attached form a carbocyclic ring of 3 to 8 carbon atoms;
$R_3$ and $R_4$ are independently hydrogen, $C_{1-3}$ alkyl, $C_{3-7}$ cycloalkyl, $C_{1-3}$ alkylthio, phenyl, phenylthio or substituted phenyl in which the substituents are V and W and when n is 2 to 3, each of the $R_3$s and $R_4$s are independently hydrogen, $C_{1-3}$ alkyl, $C_{3-7}$ cycloalkyl or only one of the $R_3$s or $R_4$s on the chain of carbons is phenyl or substituted phenyl;

$R_5$ is hydrogen, tosylate, OT, $C_{1-5}$alkyl or $C_{1-5}$alkyl substituted with tosylate or OT, $C_{3-7}$ cycloalkyl or $C_{3-7}$ cycloalkyl substituted with $C_{1-3}$ alkyl, tosylate or OT; $C_{2-5}$ alkenyl, phenyl or substituted phenyl in which the substituents are V and W, or $R_5$ is a group selected from:
(a) $C_{1-5}$-alkanoyloxy-$C_{1-4}$-alkyl,
(b)

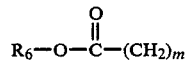

in which m is 0 to 3 and $R_6$ is $C_{1-5}$ alkyl;
(c)

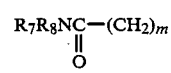

in which $R_7$ and $R_8$ are independently $C_{1-5}$ alkyl or $R_7$ and $R_8$ together with the nitrogen atom to which they are attached form a heterocycle selected from piperidinyl, morpholinyl, pyrrolidinyl, piperazinyl or thiomorpholinyl;
(d)

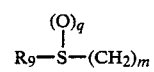

in which q is 0 to 2 and $R_9$ is $C_{1-5}$ alkyl or phenyl or substituted phenyl in which the substituents are V and W;
V and W independently are hydrogen, halogen, hydroxy, trifluoromethyl, $C_{1-3}$ alkyl, $C_{1-3}$ alkyloxy and TO—$C_{1-3}$ alkyl;
T is tert-butyldimethylsilyl, tert-butyldiphenylsilyl, trimethylsily, triethylsilyl, triisopropylsilyl or tetrahydropyranyl;
with a halogenating agent such as phenylselenyl chloride, phenylselenyl bromide or phenylsulfinyl chloride in an inert solvent at about −80° C. then treating the product with an oxidizing agent such as hydrogen perioxide or a peroxyacid in an ethereal solvent at ambient temperature to yield a compound (1-3);

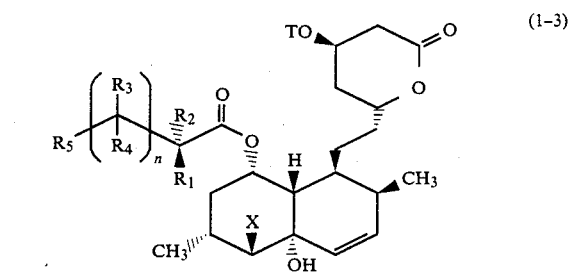

wherein X is Cl or Br;
(B) reacting the compound (1-3) with nitrosyl chloride and a base to yield a compound (1-4);

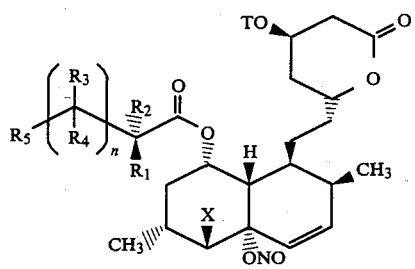

(1-4)

(C) irradiating the compound (1-4) with light to obtain compound (1-5);

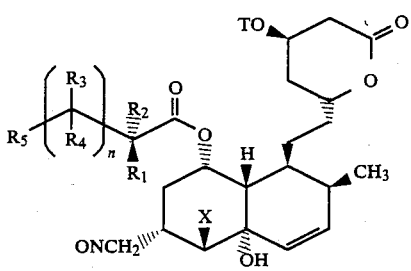

(1-5)

(D) heating the compound (1-5) in a protic solvent to afford compound (1-6);

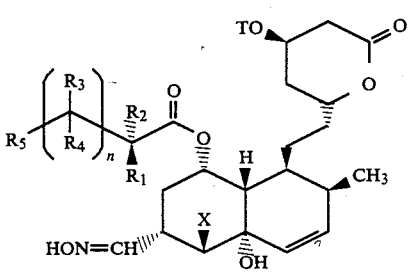

(1-6)

(E) treating compound (1-6) with an aqueous paraformaldehyde solution in the presence of an acid catalyst to yield a compound (1-7);

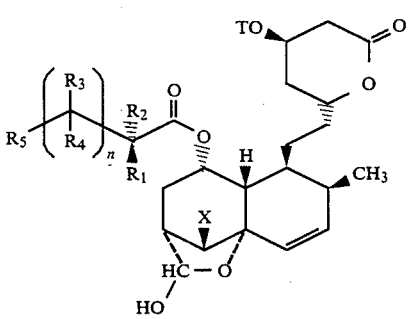

(1-7)

(F) contacting compound (1-7) with a reducing agent such as sodium borohydride or lithium borohydride in an ethereal solvent such as tetrahydrofuran to yield a compound (1-8);

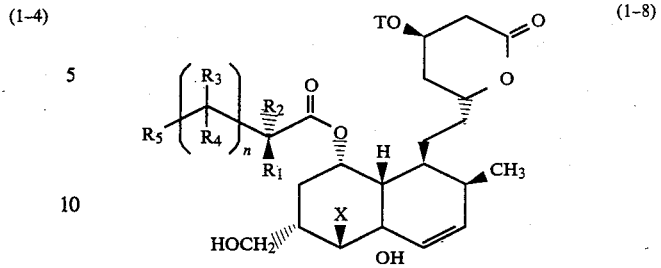

(1-8)

(G) treating the compound (1-8) with a trialkyltin hydride such as tributyltin hydride or a triaryltin hydride such as triphenyltin hydride and a radical initator such as azobisisobutyronitrile (AIBN) to yield a compound (H);

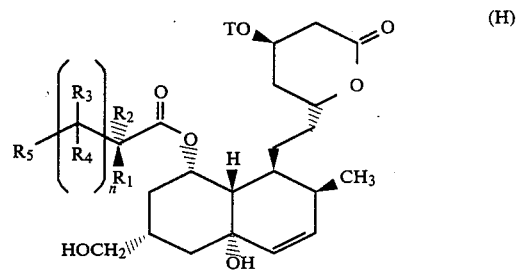

(H)

(H) treating compound (H) with an acid/polar solvent mixture to afford product (I);

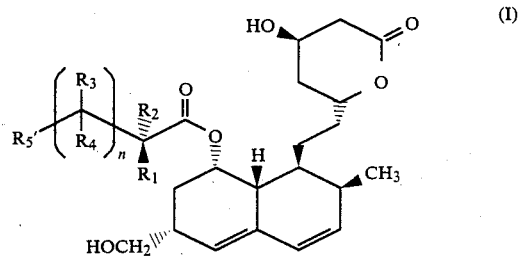

(I)

wherein $R_5'$ is identical to $R_5$ except that any OT protecting group is hydrolyzed to OH.

Alternatively products (I) may be prepared by the related process of scheme 2. In scheme 2 the halide moiety at the 5-position of the octahydronaphthyl moiety is reduced at an earlier stage in the process before nitrosyl chloride substitution and rearrangement. Each step of scheme 2 is related to a step in scheme 1. For example step G' of scheme 2 uses approximately the same conditions and accomplishes the same result, i.e. replacement of X by H, as step G of scheme 1. Step (B' and C') of scheme 2 uses the conditions of steps B and C of scheme 1.

It should be understood that the alkyl, alkylthio, alkenyl and alkanoyl groups of this invention may either be in a straight chain or branched configuration.

One embodiment of this invention is the compounds of formula (H):

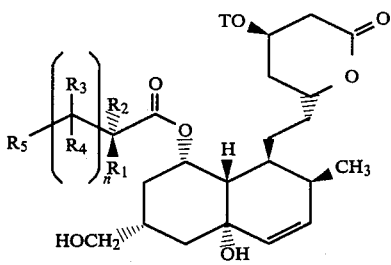

(H)

wherein n, $R_1$, $R_2$, $R_3$, $R_4$, $R_5$ and T are defined above. In one class of this embodiment are the compounds of formula (H) wherein:

$R_1$ is methyl;
$R_2$ is hydrogen or methyl;
$R_3$ and $R_4$ are independently hydrogen or $C_{1-3}$alkyl.

In a subclass:

$R_5$ is hydrogen, tosylate, OT, $C_{1-5}$alkyl, phenyl or substituted phenyl in which the substituents are V and W; and
T is tert-butyldimethylsilyl.

Exemplifying this subclass are compounds (H) wherein:

(1) n is 0, $R_2$ is methyl, $R_5$ is ethyl;
(2) n is 0, $R_2$ is hydrogen, $R_5$ is ethyl.

A second embodiment of this invention is the process for the preparation of compounds (H) from lactol intermediates of formula (1-7)

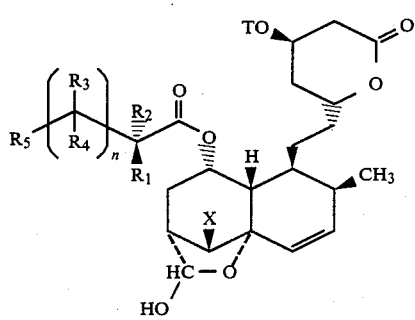

(1-7)

wherein X=Br of Cl; or from lactol intermediates (2-7).

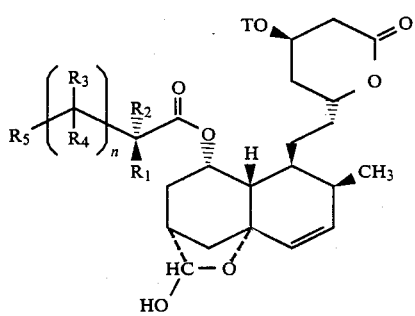

(2-7)

The process from compound (1-7) consists in contacting (1-7) with a borohydride reducing agent such as $NaBH_4$ followed by treatment with a trialkyl or triaryltin hydride such as tributyltin hydride. The process from compound (2-7) consists in contacting (2-7) with a borohydride reducing agent such as $NaBH_4$. Intermediate (1-7) is prepared as shown in the process leading from (2)→(1-7) in scheme 1; intermediate (2-7) is prepared as shown in the process leading from (2)→(2-7) in scheme 2.

A third embodiment of the present invention is the process for the preparation of products (I) from intermediates (H). This process consists in contacting a compound of formula (H) with an aqueous acid such as hydrofluoric acid in a polar solvent, such as acetonitrile.

In a general description of scheme 1 the diene (2) of step (A) is treated with a halogenating agent such as phenylselenyl chloride or bromide or phenylsulfinyl chloride, preferably phenylselenyl chloride, in an approximately equimolar ratio in an inert solvent at about $-80°$ C., for approximately 20 minutes; illustrative of such inert solvents are methylene chloride, ether and the like. After a standard workup the product residue is dissolved in an ethereal solvent, chilled to about 0° C. and oxidized with an agent such as 30% hydrogen peroxide or a peroxy acid such as peroxybenzoic acid to yield a halohydrin analog (1-3).

Compound (1-3) is treated with nitrosyl chloride at a temperature between $-10°$ and 10° C., preferably 0° C. for several minutes in a basic solvent until TLC analysis of an aliquot showed the reaction to be complete. Illustrative of such basic solvents are pyridine and quinoline and the like.

The irradiation of a compound of formula (1-4) is conducted using light of wavelength greater than 320 Å. One source of the irradiation is a medium pressure mercury lamp, at a temperature between 0° and 30° C., preferably at about 20° C., for a period of from 0.5 to 5 hours, most preferably about 0.7 hours at 20° C., in an inert solvent such as benzene, pyridine, hexane or the like, or a mixture of inert solvents.

The rearrangements of a compound of formula (1-5) to a compound of formula (1-6) is conducted at a temperature between 60° and 100° C., preferably at 80° C. for a period of 0.5 to 10 hours, most preferably for 1 hour at about 80° C., in a protic solvent and an amine base. Illustrative of such protic solvents are alcohols such as isopropanol or 2-butanol and the like. Examples of amine bases are pyridine, triethylamine, quinoline, and the like.

The conversion of an oxime (1-6) to a lactol (1-7) is conducted using an approximately 40% aqueous paraformaldehyde solution and a carboxylic acid such as acetic acid.

The lactol (1-7) is treated with a reducing agent such as an alkali metal borohydride, preferably $NaBH_4$, in an ethereal solvent, preferably tetrahydrofuran, at about 0° C. for about 1 hour.

Intermediate (1-8) is treated with a halide reducing agent such as a trialkyltin hydride or a triaryltin hydride, preferably tri-n-butyltin hydride, and a radical initator such as azobisisobutyronitrile (AIBN) in an inert solvent such as benzene at a temperature between 70° C. and 100° C. preferably about 90° C. for 0.5 to 5 hours, preferably 2 hours.

Intermediate (H) is dehydrated and the silyl ether or tetrahydropyranyl protecting groups removed by treatment with an acid in a polar solvent such as $HF/CH_3CN$ or perchloric acid/$CH_3CN$, or p-toluenesulfonic acid/$CH_3CN$ preferably hydrofluoric acid in acetonitrile, most preferably 48% hydrofluoric acid in acetonitrile, at 0° to 60° C., preferably 55°-60° C. for about 1 hour.

Each reaction of scheme 2 is found in scheme 1 and the descriptions of scheme 1 above are repeated for scheme 2. The only difference of the two schemes is the timing of the halide removal step with a trialkyltin hydride.

Starting material (2) wherein the acyl side chain is 2-methylbutyryloxy is obtained from lovastatin by reaction with a hydroxyl protecting group compound, preferably a trialkylsilyl chloride such as tert-butyldimethylsilyl chloride following the procedure in U.S. Pat. No. 4,444,784. Lovastatin is prepared according to the fermentation procedure disclosed in U.S. Pat. No. 4,231,938.

Starting compounds (2) wherein the acyl side chain is other than 2-methylbutyryloxy are prepared from lovastatin by hydrolysis of the 8-acyl side chain, following the procedure in U.S. Pat. No. 4,444,784, followed by acylation with an appropriate alkanoyl chloride in the presence of lithium bromide and dimethylaminopyridine in pyridine using the procedure in copending U.S. application Ser. No. 038,580 filed Apr. 15, 1987. Alternatively, the acylation is conducted with an alkanoyl chloride or an alkanoic acid under standard reaction conditions. The alkanoyl chloride can be formed by standard chemical transformations such as substitution with an alkyl moiety or other appropriate electrophile at an acidic C—H site on an available starting material.

The following examples illustrate the present invention and as such are not to be considered as limiting the invention set forth in the claims appended hereto.

EXAMPLE 1

Preparation of 6(R)-[2-[6(R)-hydroxymethyl-8(S)-(2,2-dimethylbutyryloxy)-2(S)-methyl-1,2,6,7,8,8a(R)-hexahydronaphthyl-1(S)]ethyl]-4(R)-hydroxy-3,4,5,6-tetrahydro-2H-pyran-2-one (I')

(a) 6(R)-[2-[5(S)-Chloro-4a(S)-hydroxy-8(S)-(2,2-dimethylbutyryloxy)-2(S),6(R)-dimethyl-1,2,4a,5,6,7,8-,8a(S)-octahydronaphthyl-1(S)]ethyl]-4(R)-(t-butyldimethylsilyloxy)-3,4,5,6-tetrahydro-2H-pyran-2-one (1-3')

A solution of phenylselenyl chloride (10 g, 52 mmol) in methylene chloride (50 ml) was added dropwise to a stirred solution of 6(R)-[2-[8(S)-(2,2-dimethylbutyryloxy)-2(S),6(R)-dimethyl-1,2,6,7,8,8a(R)-hexahydronaphthyl-1(S)]ethyl]-4(R)-(t-butyldimethylsilyloxy)-3,4,5,6-tetrahydro-2H-pyran-2-one (25.2 g, 48 mmol) in methylene chloride (350 ml) cooled in a dry ice/i-propanol bath (31 78° C.). The resulting mixture was stirred at −78° C. for 20 minutes, poured into cold water (300 ml) and extracted with ether twice (400 ml, then 150 ml). The combined extracts were dried (MgSO$_4$), filtered and concentrated to afford an oily residue which was dissolved in tetrahydrofuran (300 ml). This solution was chilled in an ice bath (0° C.), and 30% hydrogen peroxide (15 ml) was added. The resulting mixture was stirred at 0° C. for 5 minutes, then warmed to room temperature and stirring continued for 1 hour. The reaction mixture was poured into cold water and extracted with chloroform three times (400 ml, then 2×100 ml). The combined extracts were dried (MgSO$_4$), filtered and concentrated to yield a residue which was purified by flash chromatography on a silica gel column. Elution with hexane:ethyl acetate (5:1/v:v) removed any impurities. Further elution with hexane:ethyl acetate (4:1/v:v) provided the title compound as a pale yellow gum which later solidified on standing: mp 117°–8° C., NMR (CDCl$_3$) δ 0.075 (3H, s), 0.08 (3H, s), 0.85 (3H, t, J=7 Hz), 0.88 (9H, s), 0.89 (3H, d, J=7 Hz), 1.15 (b 3H, s), 1.16 (3H, s), 1.32 (3H, d, J=7 Hz), 1.58 (2H, q, J=7 Hz), 3.39 (H, s), 4.05, (H, bs), 4.30 (H, m), 4.60 (H, m), 5.32 (H, m), 5.59 (H, d, J=11 Hz), 5.79 (H, d of d, J=11, 6 Hz).

Anal. Calc'd for C$_{31}$H$_{53}$ClO$_6$Si: C, 63.61; H, 9.13. Found: C, 63.80; H, 9.04.

(b) 6(R)-[2-[5(S)-Chloro-4a(S)-nitrosyloxy-8(S)-(2,2-dimethylbutyryloxy)-2(S),6(R)-dimethyl-1,2,4a,5,6,7,8-,8a(S)-octahydronaphthyl-1(S)]ethyl]-4(R)-(t-butyldimethylsilyloxy)-3,4,5,6-tetrahydro-2H-pyran-2-one (1-4')

Nitrosyl chloride gas was passed through a solution of compound 1-3' (4 g, 6.83 mmol) in pyridine (40 ml) at 0° C. for several minutes and the reaction became a dark brown colored mixture. An aliquot was taken and partitioned between ether and water. When TLC analysis[1] of the ether layer indicated the reaction to be complete, the reaction mixture was poured into an ice/water mixture (ca. 100 ml) and extracted with benzene (150 ml). The organic phase was separated and the aqueous phase was extracted with another portion of benzene (50 ml). The combined extracts were then dried (MgSO$_4$) and filtered. The filtrate[2] was diluted with benzene to a volume of ca. 530 ml and used immediately in the subsequent photolysis.

[1] When eluted with hexane:ethyl acetate (v:v/4:1), the R$_f$ values of the starting compound 1-3' and product 1-4' are 0.25 and 0.39, respectively.
[2] The amount of pyridine present in this solution was not determined. The presence of pyridine is critical for the stabilization of compound 1-4'.

(c) 6(R)-[2-[5(S)-Chloro-4a(S)-hydroxy-8(S)-(2,2-dimethylbutyryloxy)-2(S)-methyl-6(S)-nitrosylmethyl-1,2,4a,5,6,7,8,8a(S)-octahydronaphthyl-1(S)]ethyl]-4(R)-(t-butyldimethylsilyloxy)-3,4,5,6-tetrahydro-2H-pyran-2-one (1-5')

A solution of compound 1-4' in benzene and pyridine, freshly prepared from compound 1-3' (4 g, 6.83 mmol) as described in step (b) was deoxygenated by bubbling nitrogen gas through the solution for 10 minutes. Then, it was irradiated (450 W Hanovia medium pressure mercury lamp, pyrex sleeve) at room temperature for 40 minutes while nitrogen continued to bubble through the solution. The photolyzed solution was transferred to a 500 ml R-B flask and concentrated in vacuo to a volume of ca. 25 ml. This residue was diluted with ether and shaken with dilute hydrochloric acid (1N, 150 ml) to remove pyridine. After washing with water (100 ml) and 5% soidum bicarbonate solution, the solution was dried (MgSO$_4$) and filtered. Evaporation of the filtrate left a residue which was purified by flash chromatography. Elution with hexane:ethyl acetate (v:v/4:1) removed minor side products. Then, elution with hexane:ethyl acetate (v:v/2:1) gave 1-5' as an off-white solid: m.p. 155°–7° C. (decomp.); NMR (CDCl$_3$) δ0.07 (3H, s), 0.08 (3H, s), 0.86 (3H, t, J=7 Hz), 0.9 (9H, s), 0.95 (3H, d, J=7 Hz), 1.18 (3H, s), 1.20 (3H, s), 2.84 (H, s), 2.91 (H, m), 4.18 (H, s), 4.30 (H, m), 4.36 (H, d of d, J=10, 7 Hz), 4.60 (H, m), 4.98 (H, d of d, J=10, 7 Hz), 5.27 (H, m), 5.56 (H, d, J=10 Hz), 6.81 (H, d of d, J=10, 6 Hz).

Anal. Calc'd for C$_{31}$H$_{52}$ClNO$_7$Si: C, 60.61; H, 8.53; N, 2.28. Found: C, 60.77; H, 8.75; N, 2.59.

(d) 6(R)-[2-[5(S)-Chloro-4a(S)-hydroxy-8(S)-(2,2-dimethylbutyryloxy)-2(S)-methyl-6(S)-hydroxyiminomethyl-1,2,4a,5,6,7,8,8a(S)-octahydronaphthyl-1(S)]ethyl]-4(R)-(t-butyldimethylsilyloxy)-3,4,5,6-tetrahydro-2H-pyran-2-one (1-6')

Pyridine (1.5 ml) was added to a stirred solution of compound 1-5′ (5.66 g, 9.21 mmol) in i-propanol (150 ml). The resulting mixture was heated at reflux for 1 hour. After cooling, the reaction mixture was concentrated in vacuo to afford the title compound as a foamy gum: NMR (CDCl$_3$) δ0.08 (3H, s), 0.90 (9H, s), 3.12 and 3.64 (H, both m), 4.30 (H, m), 4.30 and 4.38 (H, both s), 4.60 (H, m), 5.28 and 5.33 (H, both m), 5.57 (H, d, J=10 Hz), 5.84 (H, d, J=10, 6 Hz), 7.21 and 7.75(H, both d, J=6 Hz), 7.32 (H, bs).

(e) 6(R)-[2-[5(S)-Chloro-6(S)-formyl-4a(S)-hydroxy-2(S)-methyl-8(S)-(2,2-dimethylbutyryloxy)-1,2,4a,5,6,7,8,8a(S)-octahydronaphthyl-1(S)]ethyl]-4(R)-(t-butyldimethylsilyloxy)-3,4,5,6-tetrahydro-2H-pyran-2-one, lactol (1-7′)

A 40% aqueous paraformaldehyde solution[3] (250 ml) and acetic acid (0.53 ml, 9.28 mmol) were added to a solution of the oxime 1-6′ (5.7 g, 9.28 mmol) in acetone (350 ml) and the cloudy reaction mixture was stirred at ambient temperature overnight. The acetone was removed in vacuo at 30° C. and the aqueous residue was extracted with ether (3×100 ml). The ether extracts were combined, washed with saturated NaHCO$_3$ solution (25 ml), H$_2$O (25 ml), brine (2×25 ml) and dried over MgSO$_4$. Filtration and evaporation in vacuo gave the crude lactol 1-7′ as a tan foam which was used in Step (f) without further purification: NMR (CDCl$_3$) δ0.87 (9H, s), 1.15 (3H, s), 1.17 (3H, s), 2.58 (2H, m), 4.28 (H, m), 4.49 (H, d, J=4 Hz), 4.56 (H, m), 5.14 (H, m), 5.39 (H, d, J=10 Hz), 5.42 (H, s), 6.14 (H, d of d, J=10, 6 Hz).

[3]40% aqueous paraformaldehyde solution was prepared by refluxing a mixture of paraformaldehyde (100 g) in H$_2$O (250 ml) for 1.5 hours (oil bath=130° C.). The reaction was cooled and filtered to remove some gelatinous polymer.

(f) 6(R)-[2-[5(S)-Chloro-4a(S)-hydroxy-6(S)-hydroxymethyl-8(S)-(2,2-dimethylbutyryloxy)-1,2,4a,5,6,7,8,8a(S)-octahydronaphthyl-1(S)]ethyl]-4(R)-(t-butyldimethylsilyloxy)-3,4,5,6-tetrahydro-2H-pyran-2-one (1-8′)

A magnetically-stirred 10% aqueous THF solution (20 mL) containing the crude lactol 1-7′ from step 1(e)(2.0 g, 3.34 mmol) was cooled to 0° C. (ice/H$_2$O bath). NaBH$_4$ (252 mg, 6.67 mmol) was added and the reaction was stirred 1 hour at 0° C. before quenching with saturated NH$_4$Cl solution (10 mL). After the resulting mixture was stirred 15 minutes at 0° C., it was poured into ether (150 mL). The ethereal extract was washed in succession with the acidified aqueous layer, H$_2$O(10 mL), saturated NaHCO$_3$ solution (25 mL), brine(2×25 mL) and then dried over MgSO. Filtration and evaporation gave the alcohol 1-8′ as a yellow foam which was purified by flash chromatography on a 5×15 cm column of silica gel (230–400 mesh). The column was eluted with acetone/methylene chloride (7.5:92.5/v:v) to provide 1-8′ as a pale yellow solid, mp 161°–4° C.: NMR (CDCl$_3$) δ0.071 (3H, s), 0.081 (3H, s), 0.85 (3H, t, J=7 Hz), 0.89 (9H, s), 1.15 (3H, s), 1.16 (3H, s), 3.17 (H, m), 3.68 (H, m), 4.03 (H, m), 4.28 (H, m), 4.29 (H, bs), 4.61 (H, m), 5.28 (H, m), 5.59 (H, d, J=10 Hz), 5.80 (H, d of d, J=10, 5 Hz).

Analysis Calc'd. for C$_{31}$H$_{53}$ClO$_7$Si: C, 61.92; H, 8.88. Found: C, 61.80; H, 9.19.

(g) 6(R)-[2-[4a(S)-hydroxy-6(R)-hydroxymethyl-8(S)-(2,2-dimethylbutyryloxy)-1,2,4a,5,6,7,8,8a(S)-octahydronaphthyl-1(S)]ethyl]-4(R)-(t)-butyldimethylsilyloxy)-3,4,5,6-tetrahydro-2H-pyran-2-one (H′)

Tributyltin hydride (1.12 mL, 4.16 mmol) and azobisisobutyronitrile (AIBN) (113 mg, 0.69 mmol) were added to a magnetically-stirred benzene solution (20 mL) of the chlorohydrin 1-8′ (1.25 g, 2.08 mmol). After the solution was heated at reflux (90° C. oil bath) for 1 hour, more tributyltin hydride (0.3 mL, 1.11 mmol) was added and heating was continued for an additional hour. The benzene was removed in vacuo and the yellow oily residue was stirred in cold (ice-water bath) pet. ether (40 mL) to give the title compond H′ as a pale yellow solid which was used in the next step without further purification. The alcohol H′ can be purified by flash chromatography on silica gel (230–400 mesh). Elution with acetone/methylene chloride (1:9/v:v) provided the compound as a colorless solid, mp 133°–5° C.: NMR (CDCl$_3$) δ0.068 (3H, s), 0.079 (3H, s), 0.85 (3H, t, J=7 Hz), 0.88 (9H, s), 1.15 (3H, s), 1.16 (3H, s), 3.67 (H, d of d, J=10, 7 Hz), 3.90 (H, d of d, J=10, 7 Hz), 4.29 (H, m), 4.60 (H, m), 5.26 (H, m), 5.58 (H, d, J=10 Hz), 5.69 (H, d of d, J=10, 6 Hz).

(h) 6(R)-[2-[6(R)-hydroxymethyl-8(S)-(2,2-dimethylbutyryloxy)-2(S)-methyl-1,2,6,7,8,8a(R)-hexahydronaphthyl-1(S)]ethyl]-4(R)-hydroxy-3,4,5,6-tetrahydro-2H-pyran-2-one (I′)

A solution of 48% aqueous HF/CH$_3$CN (1:19/v:v, 24 mL) was added to a magnetically stirred acetonitrile solution (24 mL) of the silyl ether H′ from step 1(g) (2.38 g, 4.2 mmol) and the resulting solution was heated at 55°–60° C. (H$_2$O bath) for 1 hour[4]. After cooling to 5° C. (ice/H$_2$O bath), the reaction was quenched with saturated NaHCO$_3$ (25 mL) and the resulting mixture was added to ether (500 mL). The ether was washed with brine (2×25 mL) and dried over MgSO$_4$. Filtration and evaporation gave the title compound I′ as a viscous oil. The product was purified by flash chromatography on a silica gel column (230–400 mesh). Elution of the column with acetone/methylene chloride (1:3/v:v) provided the product as a colorless foam. nmr (CDCl$_3$) δ0.84 (3H, t, J=7 Hz), 0.90 (3H, d, J=7 Hz), 1.12 (3H, s), 1.13 (3H, s), 3.51 (H, m), 3.62 (H, m), 4.39 (H, m), 4.62 (H, m), 5.40 (H, m), 5.60 (H, m), 5.82 (H, d of d, J=10, 6 Hz), 6.01 (H, d, J=10 Hz).

Analysis Calc'd for C$_{25}$H$_{38}$O$_6$.0.5H$_2$O. C, 67.69, H, 8.86. Found: C, 68.02; H, 8.81.

[4]The reaction was monitored by TLC [Whatman Silica gel 60A, acetone/methylene chloride (1:4/v:v)] R$_f$ of H′=0.58, R$_f$ of I′=0.18.

EXAMPLE 2

Preparation of 6(R)-[2-[6(R)-hydroxymethyl-8(S)-(2,2-dimethylbutyryloxy)-2(S)-methyl-1,2,6,7,8,8a(R)-hexahydronaphthyl-1(S)]ethyl-4(R)-hydroxy-3,4,5,6-tetrahydro-2H-pyran-2-one (I′)

(a) 6(R)-[2-[5(S)-Chloro-4a(S)-hydroxy-8(S)-(2,2-dimethylbutyryloxy)-2(S),6(R)-dimethyl-1,2,4a,5,6,7,8,8a(S)-octahydronaphthyl-1(S)]ethyl]-4(R)-(t-butyldimethylsilyloxy)-3,4,5,6-tetrahydro-2H-pyran-2-one (2-3′)

A solution of phenylselenyl chloride (10 g, 52 mmol) in methylene chloride (50 ml) was added dropwise to a stirred solution of 6(R)-[2-[8(S)-(2,2-dimethylbutyryloxy)-2(S),6(R)-dimethyl-1,2,6,7,8,8a(R)-hexahydronaphthyl-1(S)]ethyl]-4(R)-(t-butyldimethylsilyloxy)-3,4,5,6-tetrahydro-2H-pyran-2-one (25.2 g, 48 mmol) in methylene chloride (350 ml) cooled in a dry ice/i-propanol bath (−78° C.). The resulting mixture was stirred at −78° C. for 20 minutes, poured into cold water (300 ml) and extracted with ether twice (400 ml, then 150 ml). The combined extracts were dried (MgSO$_4$), filtered and concentrated to afford an oily residue which was dissolved in tetrahydrofuran (300 ml). This solution was chilled in an ice bath (0° C.), and 30% hydrogen peroxide (15 ml) was added. The resulting mixture was stirred at 0° C. for 5 minutes, then warmed to room temperature and stirring continued for 1 hour. The reaction mixture was poured into cold water and extracted with chloroform three times (400 ml, then 2×100 ml). The combined extracts were dried (MgSO$_4$), filtered and concentrated to yield a residue which was purified by flash chromatography on a silica gel column. Elution with hexane:ethyl acetate (5:1/v:v) removed any impurities. Further elution with hexane:ethyl acetate (4:1/v:v) provided the title compound as a pale yellow gum which later solidified on standing: mp 117°–8° C., NMR (CDCl$_3$) δ0.075 (3H, s), 0.08 (3H, s), 0.85 (3H, t, J=7 Hz), 0.88 (9H, s), 0.89 (3H, d, J=7 Hz), 1.15 (3H, s), 1.16 (3H, s), 1.32 (3H, d, J=7 Hz), 1.58 (2H, q, J=7 Hz), 3.39 (H, s), 4.05, (H, bs), 4.30 (H, m), 4.60 (H, m), 5.32 (H, m), 5.59 (H, d, J=11 Hz), 5.79 (H, d of d, J=11, 6 Hz).

Anal. Calc'd for C$_{31}$H$_{53}$ClO$_6$Si: C, 63.61; H, 9.13. Found: C, 63.80; H, 9.04.

(b) 6(R)-[2-[4a(S)-Hydroxy-8(S)-(2,2-dimethylbutyryloxy-2(S),6(R)-dimethyl-1,2,4a,5,6,7,8,8a(S)-octahydronaphthyl-1(S)]-ethyl]-4(R)-(t-butyldimethylsilyloxy)-3,4,5,6-tetrahydro-2H-pyran-2-one (2-4′)

Tributyltin hydride (1.2 ml, 4.5 mmol) and azabisisobutyronitrile) AIBN (150 mg, 0.9 mmol), were added to a solution of chlorohydrin 2-3′ (1.5 g, 2.6 mmol) in benzene (50 ml). The resulting mixture was heated at reflux for 3 hours. After cooling, the reaction mixture was concentrated and the residue was purified by flash chromatography on a silica gel column. The impurities were removed by elution with 10% ethyl acetate in hexane. Further elution with hexane:ethyl acetate (3:1/v:v) gave the desired product (2-4′) as a white solid: mp 103°–4°; NMR (CDCl$_3$) δ0.08 (3H, S), 0.09 (3H, S), 0.89 (9H, S), 0.94 (3H, J=7 Hz), 1.16 (3H, S), 1.17 (3H, S), 4.29 (H, m), 4.58 (H, m), 5.30 (H, m), 5.58 (H, d, J=10 Hz), 5.65 (H, d of d, J=10, 6 Hz).

Anal. Calcd for C$_{31}$H$_{54}$O$_6$Si: C, 67.59; H, 9.88. Found: C, 67.20; H, 9.99.

(c) 6(R)-[2-[4a(S)-hydroxy-8(S)-(2,2-dimethylbutyryloxy)-2(S)-methyl-6(R)-nitrosylmethyl-1,2,4a,5,6,7,8a-(S)-octahydronaphthyl-1(S)]ethyl]-4(R)-(t-butyldimethylsilyloxy)-3,4,5,6,-tetrahydro-2H-pyran-2-one (2-5′)

Nitrosyl chloride gas was bubbled through a stirred solution of compound 2-4′ (1.25 g, 2.27 mmol) in pyridine (25 ml) at 0° C. for several minutes until the reaction mixture became dark brown colored. An aliquot was taken and partitioned between ether and water. If TLC analysis[1] of the ether layer indicated the completion of the reaction, the reaction mixture was poured into an ice/water mixture (50 ml) and extracted with benzene (50 ml). The aqueous phase was separated and extracted with benzene (25 ml). The combined extracts were dried and filtered.

[1]When eluted with hexane:ethyl acetate (v:v/4:1), the R$_f$ values of the starting compound 2-4′ and product 2-5′ are 0.2 and 0.32, respectively.

This filtrate was diluted with benzene to a volume of 410 ml, and transferred to a photoreactor. It was deoxygenated by bubbling nitrogen gas through the solution for 10 minutes. Then, it was irradiated (450 w Hanovia medium pressure mercury lamp, pyrex sleeve) at room temperature for 0.5 hour while nitrogen gas continued to bubble through the solution. The photolyzed solution was transferred to a round bottom flask, and concentrated on a rotary evaporator followed by evaporation under high vacuum. The residue was then purified by flash chromatography on a silica gel column. Impurities were removed by elution with hexane:ethyl acetate (3:1/v:v to 1.5:1/v:v). Further elution with hexane:ethyl acetate (1:1/v:v) provided 6(R)-[2-[4a(S)-hydroxy-8(S)-(2,2-dimethylbutyryloxy)-2(S)-methyl-6(R)-hydroxyiminomethyl-1,2,4a,5,6,7,8,8a-(S)-octahydronaphthyl-1(S)]ethyl]-4(R)-(t-butyldimethylsilyloxy)-3,4,5,6-tetrahydro-2H-pyran-2-one 2-6′ (NMR spectrum reported in the next step) and the titled compound 2-5′: NMR (CDCl) δ0.075 (3H, S), 0.085 (3H, S), 0.88 (9H, S), 1.19 (3H, S), 1.20 (3H, S), 2.68 (H, S), (4.29 (H, M), 4.33 (H, d of d, J=11, 7 Hz), 4.59 (H, m), 4.97 (H, d of d, J=H, 7 Hz), 5.25 (H, m), 5.55 (H, d, J=10 Hz), 5.67 (H, d of d, J=10, 6 Hz).

(d) 6(R)-[2-[4a(S)-hydroxy-8(S)-(2,2-dimethylbutyryloxy)-2(S)-methyl-6(R)-hydroxyiminomethyl-1,2,4a,5,6,7,8,8a(S)-octahydronaphthyl-1(S)]ethyl]-4(R)-(t-butyldimethylsilyloxy)-3,4,5,6-tetrahydro-2H-pyran-2-one (2-6′)

Pyridine (0.1 ml) was added to a stirred solution of compound 2-5′ (0.60 g, 1.03 mmol) in i-propanol (15 ml). The resulting mixture was heated at reflux (steam bath) for 40 minutes. After cooling, the reaction mixture was concentrated in vacuo to afford the title compound as a foamy gum: NMR (CDCl$_3$) δ0.08 (3H, S), 0.09 (3H, s), 0.89 (9H S), 2.83 and 3.40 (H, both m), 4.30 (H, m), 4.60 (H, m), 5.25 and 5.32 (H, both m), 5.69 (H, d, J=10 Hz), 5.70 (H, d of d, J=10, 6 Hz), 7.40 and 7.67 (H, both d, J=6 Hz), 8.50 (H, bs).

(e) 6(R)-[2-[6(R)-formyl-4a(S)-hydroxy-2(S)-methyl-8(S)-(2,2-dimethylbutyryloxy)-1,2,4a,5,6,7,8,8a(S)-octahydronaphthyl-1(S)]ethyl]-4(R)-(t-butyldimethylsilyloxy)-3,4,5,6-tetrahydro-2H-pyran-2-one, lactol (2-7′)

A 40% aqueous paraformaldehyde[2] solution (35 ml) and acetic acid (68 μl, 1.19 mmol) were added to a solution of the oxime (2-6′) (690 mg, 1.19 mmol) in acetone (45 ml) and the cloudy reaction mixture was stirred at ambient temperature overnight. NMR analysis of an aliquot showed that oxime was still present. Acetic acid (68 μl, 1.19 mmol) was added and the reaction mixture was stirred at ambient temperture for another 24 hours. The acetone was removed in vacuo at 30° C. and the aqueous residue was extracted with ether (3×100 ml). The ether extracts were combined, washed with brine (2×25 ml) and dried over MgSO$_4$. Filtration and evaporation in vacuo gave the crude lactol (2-7′) as a viscous oil which was used in Step (f) without further purification. NMR (CDCl$_3$) δ0.059 (3H, S), 0.070 (3H, S), 0.87 (9H, S), 1.16 (3H, S), 1.17 (3H, S), 4.28 (H, m), 4.55 (H, m), 5.20 (H, m), 5.30 and 5.38 (H, S), 5.50 (H, d, J=10 Hz), 6.00 and 6.12 (H, d of d, J=10, 6 Hz).

[2]40% aqueous paraformaldehyde solution was prepared by refluxing a mixture of paraformaldehyde (100 g) in H$_2$O (250 ml) for 1.5 hours (oil bath=130° C.). The reaction was cooled and filtered to remove some gelatinous polymer.

(f) 6(R)-[2-[4a(S)-hydroxy-6(R)-hydroxymethyl-2(S)-methyl-8(S)-2,2-dimethylbutyryloxy)-1,2,4a,5,6,7,8-,8a(S)-octahydronaphthyl-1(S)]ethyl]-4(R)-(t-butylmethylsilyloxy)-3,4,5,6-tetrahydro-2H-pyran-2-one (H′)

A magnetically stirred 10% aqueous THF solution (20 ml) of the crude lactol (2-7′) (contaminated with paraformaldehyde [860 mg, 1.19 mmol (max.)] was cooled to 0° C. (ice/H$_2$O bath) NaBH$_4$ (90 mg, 2.38 mmol) was added and the reaction was stirred at 0° C. for 1 hour. TLC[3] analysis showed that some lactol was still present so more NaBH$_4$ (45 mg, 1.19 mm) was added and stirring was continued for about 30 minutes and then quenched with saturated NH₄Cl solution (5 ml). The resulting mixture was stirred for 10 minutes at 0° C. and poured into ether (100 ml). The ether was washed with the acidified aqueous layer, brine (2×10 ml) and dried over MgSO₄. Filtration and evaporation gave the crude alcohol H' as a viscous yellow oil. The alcohol H' was purified by flash chromatography on a 4×15 cm column of silica gel (230-400 mesh). Elution of the column with acetone/methylene chloride (1:9/V:V) provided the purified product as a colorless solid. mp 133°-5° C. NMR (CDCl₃) δ0.068 (31, S), 0.070 (3H, S), 0.85 (3H, t, J=7 Hz), 0.88 (9H, S), 1.15 (3H, S), 1.16 (3H, S), 3.67 (H, d of d, J=10, 7 Hz), 3.90 (H, d of d, J=10, 7 Hz), 4.29 (H, m), 4.60 (H, m), 5.27 (H, m), 5.58 (H, d, J=10 Hz), 5.69 (H, d of d, J=10, 6 Hz).

³The reaction was followed by TLC [Whatman Silica gel 60 A, acetone/methylene chloride (1:9/v:v) R_f of (2-7')=0.42, R_f of H'=0.25.

(g) 6(R)-[2-[6(R)-hydroxymethyl-8(S)-(2,2-dimethylbutyryloxy)-2(S)-methyl-1,2,6,7,8,8a(R)-hexahydronaphthyl-1(S)]ethyl]-4(R)-hydroxy-3,4,5,6-tetrahydro-2H-pyran-2-one A solution of 48% aqueous HF/CH₃CN (1:19/v:v, 24 mL) was added to a magnetically stirred acetonitrile solution (24 mL) of the silyl ether H' from step 2(f) (2.38 g, 4.2 mmol) and the resulting solution was heated at 55°-60° C. (H₂O bath) for 1 hour⁴. After cooling to 5° C. (ice/H₂O bath), the reaction was quenched with saturated NaHCO₃ (25 mL) and the resulting mixture was added to ether (500 mL). The ether was washed with brine (2×25 mL) and dried over MgSO₄. Filtration and evaporation gave the title compound I' as a viscous oil. The product was purified by flash chromatography on a silica gel column (230-400 mesh). Elution of the column with acetone/methylene chloride (1:3/v:v) provided the product as a colorless foam. NMR (CDCl₃) δ0.84 (3H, t, J=7 Hz), 0.90 (3H, d, J=7 Hz), 1.12 (3H, s), 1.13 (3H, s), 3.51 (H, m), 3.62 (H, m), 4.39 (H, m), 4.62 (H, m), 5.40 (H, m), 5.60 (H, m), 5.82 (H, d of d, J=10, 6 Hz), 6.01 (H, d, J=10 Hz).

Analysis Calc'd for C₂₅H₃₈O₆.0.5H₂O. C, 67.69, H, 8.86. Found: C, 68.02; H, 8.81.

⁴The reaction was monitored by TLC [Whatman Silica gel 60A, acetone/methylenchloride (1:4/v:v)] R_f of H'=0.58, R_f of I'=0.18.

What is claimed is:

1. A compound of structural formula (H):

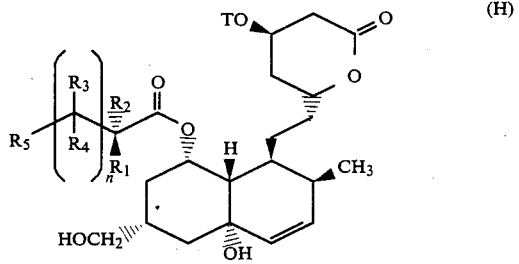

wherein
n is 0 to 3;
R₁ and R₂ independently are hydrogen, C₁₋₅alkyl, or R₁ and R₂ together with the carbon atom to which they are attached form a carbocyclic ring of 3 to 8 carbon atoms;
R₃ and R₄ are independently hydrogen, C₁₋₃ alkyl, C₃₋₇ cycloalkyl, C₁₋₃ alkylthio, phenyl, phenylthio or substituted phenyl in which the substituents are V and W and when n is 2 to 3, each of the R₃s and R₄s are independently hydrogen, C₁₋₃ alkyl, C₃₋₇ cycloalkyl or only one of the R₃s or R₄s on the chain of carbons is phenyl or substituted phenyl;
R₅ is hydrogen, tosylate, OT, C₁₋₅alkyl or C₁₋₅alkyl substituted with tosylate or OT, or C₃₋₇cycloalkyl or C₃₋₇cycloalkyl; substituted with C₁₋₃alkyl, tosylate or OT, C₂₋₅ alkenyl, phenyl or substituted phenyl in which the substituents are V and W, or R₅ in a group selected from:
(a) C₁₋₅-alkanoyloxy-C₁₋₄-alkyl,
(b)

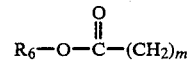

in which m is 0 to 3 and R₆ is C₁₋₅ alkyl;
(c)

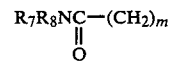

in which R₇ and R₈ are independently C₁₋₅ alkyl or R₇ and R₈ together with the nitrogen atom to which they are attached form a heterocycle selected from piperidinyl, morpholinyl, pyrrolidinyl, piperazinyl or thiomorpholinyl;
(d)

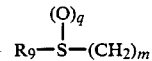

in which q is 0 to 2 and R₉ is C₁₋₅alkyl or phenyl or substituted phenyl in TO-C₁₋₃alkyl which the substituents are V and W;
V and W independently are hydrogen, halogen, hydroxy, trifluoromethyl, C₁₋₃alkyl, C₁₋₃alkyloxy and TO-C₁₋₃alkyl;
T is tert-butyldimethylsilyl, tert-butyldiphenylsilyl, trimethylsilyl, triethylsilyl, triisopropylsilyl or tetrahydropyranyl.

2. A compound of claim 1 wherein:
R₁ is methyl;
R₂ is hydrogen or methyl;
R₃s and R₄s are independently hydrogen or C₁₋₃alkyl.

3. A compound of claim 2 wherein:
R₅ is hydrogen, tosylate, OT, C₁₋₅ alkyl, phenyl or substituted phenyl in which the substituents are V and W; and
T is tert-butyldimethylsilyl.

4. A compound of claim 3 selected from the group wherein:
(a) n is 0, R₂ is methyl, R₅ is ethyl;
(b) n is 0, R₂ is hydrogen, R₅ is ethyl.

* * * * *